US005491081A

United States Patent [19]
Webb

[11] Patent Number: 5,491,081
[45] Date of Patent: Feb. 13, 1996

[54] SOYBEAN CYST NEMATODE RESISTANT SOYBEANS AND METHODS OF BREEDING AND IDENTIFYING RESISTANT PLANTS

[75] Inventor: David M. Webb, Johnston, Iowa

[73] Assignee: Pioneer Hi-Bred International, Inc., Des Moines, Iowa

[21] Appl. No.: 187,569

[22] Filed: Jan. 26, 1994

[51] Int. Cl.[6] .......................... G01N 21/76; C07H 21/00; A01H 1/04; A01H 5/00; A01C 1/00
[52] U.S. Cl. ..................................... 435/172.3; 435/172.1; 435/6; 536/23.1; 800/200; 800/205; 800/255; 800/DIG. 26; 47/58; 47/DIG. 1
[58] Field of Search ...................... 47/58.07, 58, DIG. 1; 800/200, 205, 250, 255, DIG. 26; 435/172.1, 6, 172.3; 536/23.1

[56] References Cited

U.S. PATENT DOCUMENTS

| | | | |
|---|---|---|---|
| 5,264,210 | 11/1993 | Novitski et al. | 424/93.47 |
| 5,270,448 | 12/1993 | Payne | 424/93.461 |

FOREIGN PATENT DOCUMENTS

| | | |
|---|---|---|
| 0568027 | 4/1993 | European Pat. Off. . |
| WO9319181 | 9/1993 | WIPO . |
| WO9318135 | 9/1993 | WIPO . |

OTHER PUBLICATIONS

Anand, et al. (1984) Identification of Additional Soybean Germ Plasm with Resistance to Race 3 of the Soybean Cyst Nematode, *The American Phytopathological Society*, vol. 68, No. 7, pp. 593–595.
Anand, et al. (1985) Soybean Genotypes with Resistance to Races of Soybean Cyst Nematode[1], *Crop Science*, vol. 25, pp. 1073–1075.
Baltazar, et al. (1992) Identification of restriction fragment length polymorphisms (RFLP's) to map soybean cyst nematode resistance genes in soybean, *Soybean Genet. Research*, vol. 19, pp. 120–122.
Boutin, et al. (1992) RFLP analysis of cyst nematode resistance in soybeans, *Soybean Genet. Research*, vol. 19, pp. 123–127.
Caldwell, et al. (1960) Inheritance of Resistance of Soybeans to the Cyst Nematode, *Heterodera Glycines*[1], *Agronomy Journal*, vol. 52, pp. 635–636.
Concibido, et al. (1993) RFLP Mapping of Cyst Nematode Resistance Genes in Soybeans, *Soybean Genet. Research*, vol. 20, pp. 136–139.

Concibido, et al. (1994) DNA Marker Analysis of Loci underlying Resistance to Soybean Cyst Nematode (*Heterodera glycines* Ichinohe), *Crop Sci.*, vol. 34, pp. 240–246.
Fehr, Walter R. (1987) Breeding Methods for Cultivar Development, *In J. R. Wilcox (Ed.) Soybeans: Improvement, Production, and Uses,* 2nd Ed., pp. 249–293.
Weidong, et al. (1989) Linkage for resistance to race 5 and race 3 of the soybean cyst nematode (Heterodera glycines) in the cross PI 437654 x Tracy M, *Soy. Gen. News*, vol. 16, pp. 165–167.
Matson, et al. (1965) Evidence of a Fourth Gene For Resistance to the Soybean Cyst Nematode[1], *Crop Science*, vol. 5, p. 477.
Myers, et al. (1991) Inheritance of resistance and genetic relationships among soybean plant introductions to races of soybean cyst nematode, *Euphytica*, vol. 55, pp. 197–201.
Myers, et al. 1989 Resistance to *Heterodera Glycines* in Soybean PI 437654, A. J. Pascale (Ed.) Proc. *4th Int. Conf. on World Soybean Res.*, Buenos Aires, pp. 1230–1234.
Rao–Arelli, et al. (1988) Genetic Relationships among Soybean Plant Introductions for Resistance to Race 3 of Soybean Cyst Nematode, *Crop Science*, vol. 28, pp. 650–652.
Rao–Arelli, et al. (1992) Soybean Resistance to Soybean Cyst Nematode Race 3 is Conditioned by an Additional Dominant Gene, *Crop Science*, vol. 32, pp. 862–864.
Weisemann, et al. (1992) Molecular markers located proximal to the soybean cyst nematode resistance gene, Rhg4, *Theot. Appl. Genet.*, vol. 85, pp. 136–138.
Walton, 1993, Seed World, pp. 22–29.
May et al. 1991, Nucleic Acids Research, 19(16):4557.
Michelmore et al. 1991, Proc. Natl. Acad. Sci USA, 88:9828–9832.
Rieger et al. 1976, In Glossary of Genetics and Cytogenetics, Classical and Molecular, p. 333.

Primary Examiner—David T. Fox
Assistant Examiner—Erich E. Veitenheimer
Attorney, Agent, or Firm—Pioneer Hi-Bred International, Inc.

[57] ABSTRACT

A method for introgressing soybean cyst nematode resistance into elite soybean germplasm is disclosed. The method involves using genetically mapped loci associated with soybean cyst nematode resistance for marker-assisted selection during introgression of soybean cyst nematode resistance into elite soybean germplasm. Also disclosed are a method for confirming selection for soybean cyst nematode resistance; quantitative trait loci associated with soybean cyst nematode resistance; and soybean lines bred to be resistant to soybean cyst nematode infestation.

10 Claims, 2 Drawing Sheets

SOYBEAN CYST NEMATODE RESISTANT SOYBEANS AND METHODS OF BREEDING AND IDENTIFYING RESISTANT PLANTS

FIELD OF THE INVENTION

This invention relates to soybeans and methods of soybean breeding. More particularly, the invention relates to soybean cyst nematode resistant soybean lines and methods of breeding same, the methods involving genetic marker analysis.

BACKGROUND OF THE INVENTION

Soybeans are a major cash crop and investment commodity in North America and elsewhere. Soybean oil is one of the most widely used edible oils, and soybeans are used worldwide both in animal feed and in human food production.

The soybean cyst nematode, *Heterodera glycines* Ichinohe, was first identified on soybeans in the United States in 1954 at Castle Hayne, N.C. Winstead, et al., Plant Dis. Rep. 39:9–11,1955. Since its discovery the soybean cyst nematode ("SCN") has been recognized as one of the most destructive pests in soybean. It has been reported in nearly all states in which soybeans are grown, and it causes major production problems in several states, being particularly destructive in the midwestern states. See generally: Caldwell, et al., Agron. J. 52:635–636,1960; Rao-Arelli and Anand, Crop. Sci. 28:650–652, 1988; Baltazar and Mansur, Soybean Genet. Newsl. 19:120–122, 1992; Concibido, et al., Crop. Sci., 1993. For example, susceptible soybean cultivars had 5.7–35.8% lower seed yields than did resistant cultivars on SCN race-3 infested sites in Iowa. Niblack and Norton, Plant Dis. 76:943–948, 1992.

Although the use of nematocides is effective in reducing the population level of the nematode, nematocide use is both uneconomical and potentially environmentally unsound as a control measure in soybean production. Neither is crop rotation a practical means of nematode control, since rotation with a nonsusceptible crop for at least two years is necessary for reducing soybean losses. Therefore, it has long been felt by soybean breeders, that use of resistant varieties is the most practical control measure.

Screening of soybean germplasm for resistance to SCN was begun soon after the discovery of the nematode in the United States, and Golden, et al. (Plant Dis. Rep. 54:544–546, 1970) have described the determination of SCN races. Although SCN was discovered in North America about 40 years ago, soybean breeding for resistance to SCN has mostly utilized genes from two plant introductions—Peking and PI88788, and while these lines have resistance genes for several SCN races, including race-3, they do not provide resistance to all known races.

The plant introduction PI437654 is the only known soybean to have resistance to SCN races-3 (Anand, Plant Dis. 68:593–595, 1984), 1, 2, 5, 14 (Anand, in Lambertin and Taylor (Eds), pp. 269–276, 1985), 6, and 9 (Rao-Arelli et al., Plant Dis. 76:894–896, 1992). However, PI437654 has black seed coat, poor standability, seed shattering, and low yield, necessitating the introgression of its SCN resistance into elite germplasm with a minimum of linkage drag. Conventional breeding with PI437654 produced the variety "Hartwig" (Anand, Crop Sci. 31:856, 1991), which is more adapted to cultivation and can be used as a source of SCN resistance in future soybean breeding.

Resistance to SCN is multigenic and quantitative in soybean (Mansur et al., Crop Sci. 1993), although complete resistance can be scored qualitatively. Myers and Anand (Euphytica 55:197–201, 1991) estimated that PI437654 has three genes required for complete resistance to SCN race-3, four genes for race-5, and three genes for race-14. The multiple genes and SCN races involved contribute to the difficulty breeders have in developing SCN resistant soybean varieties.

Breeding programs for SCN resistance rely primarily on field evaluations where natural nematode populations occur. However, these populations can be mixtures of undetermined races (Young, Crop Sci. 22:385–388, 1982) and the environment can vary, thereby affecting the overwintering and infection capability of the nematodes (Niblack and Norton, Plant Dis. 76:943–948, 1992). Although evaluations using inbred nematode populations in controlled greenhouse environments are superior, they are prohibitively expensive, and the nematodes are difficult to manage for large breeding programs. These deficiencies in each evaluation method make SCN resistance a difficult trait for soybean improvement.

Genetic markers closely linked to important genes may be used to indirectly select for favorable alleles more efficiently than direct phenotypic selection (Lande and Thompson, Genetics 124:543–546, 1990). The i allele at the I locus, responsible for black or imperfect black seed-coat type, is closely linked in coupling to the SCN resistance allele, $Rhg_4$ in the variety Peking (Matson and Williams, Crop Sci. 5:477, 1965). The I locus was mapped to linkage group VII of the classical genetic map (Weiss, Crop. Sci. 10:627–629, 1970) and to linkage group A of the public RFLP map (Keim et al., Proc. 4th World Soy. Res. Conf., 1989). In addition, other SCN race-3 resistance loci have been associated with RFLP markers and tentatively mapped to linkage group B or G (Boutin et al., Soybean Genet. Newsl. 19:120–122, 1992) and possibly K (Concibido et al., Crop Sci., in press) using the germplasm source PI209332.

Therefore, it is of particular importance, both to the soybean breeder and to farmers who grow and sell soybeans as a cash crop, to identify, through genetic mapping, the quantitative trait loci (QTL) for resistance to the various SCN races. Knowing the QTLs associated with resistance to the SCN races, soybean breeders will be better able to breed SCN resistant soybeans which also possess the other genotypic and phenotypic characteristics required for commercial soybean lines.

SUMMARY OF THE INVENTION

The present invention provides a method of introgressing SCN resistance into non-resistant soybean germplasm. Loci associated with SCN resistance in soybean lines known to be resistant to SCN are used in marker assisted selection during introgression of SCN resistance into elite soybean germplasm. Examples of soybean lines known to be resistant to one or more races of SCN include PI437654, Peking, and PI90763. The method of the present invention can be used to breed soybeans resistant to any SCN race. The SCN races of particular commercial importance are races-3, 1, 2, 5, 14, 6 and 9.

The method of the present invention comprises the use of nucleic acid markers genetically linked to loci associated with SCN resistance in lines known to be resistant to one or more SCN races. The markers are used in genetic mapping of genetic material of soybean lines to be used in and/or which have been developed in a breeding program, allowing for marker-assisted selection during introgression of SCN resistance into elite germplasm.

According to the method of the invention, any art-recognized genetic mapping techniques may be utilized, with preferred embodiments utilizing Restriction Fragment Length Polymorphism (RFLP) mapping, RAPD mapping, or microsatellite mapping, using the nucleic acid markers recognized or applicable to the particular method(s). Markers useful in genetic mapping, and in a particular embodiment in RFLP mapping, include, for example, the following: pA85a, php02302a, php02340a, pk400a, pt155a, pBLT24a, php05180a, pSAC3a, or pA111b for linkage group A; php02366a, php02361a, UBC440a, pK69a, or pL50b for linkage group G; and pA226a, pA715a, pk24a, pB157b, php02275a, UBC379a, OPC-04a, or php02301a for linkage group M. Markers useful in the practice of the method of the present invention in an embodiment utilizing RAPD mapping include, for example, UBC440 for linkage group G and UBC379a and OPC-04a for linkage group M.

An alternative embodiment of the present invention comprises a method of confirming selection for SCN resistance. This embodiment comprises identifying products of a soybean breeding program having in their genetic material the loci associated with resistance to one or more SCN races.

A further embodiment of the present invention comprises the quantitative trait loci (QTL) associated with SCN resistance. The loci of the invention are mapped (or identified or defined) using particular nucleic acid markers, as discussed above, and are further defined by their association with particular art-recognized linkage groups.

An additional embodiment of the present invention comprises soybeans resistant to the various SCN races bred according to the method of the present invention, or developed through the identification of parental lines possessing one or more of the QTL of the invention.

DETAILED DESCRIPTION OF THE INVENTION

The present invention relates to a novel and useful method for introgressing, in a reliable and predictable manner, SCN resistance into non-resistant soybean germplasm. The method involves the genetic mapping of loci associated with SCN resistance. SCN race resistance can be determined in any acceptable manner; preferably in greenhouse conditions using a homogeneous population of the particular SCN race.

The soybean line selected for mapping is subjected to DNA extraction. In a preferred embodiment the CTAB method (Murray and Thompson, Nucl. Acids Rev. 8:4321–4325, 1980; Keim et al., Soybean Genet. Newsl. 15:150–152, 1988) is used. Nucleic acid probes are used as markers in mapping the resistance loci, and appropriate probes are selected based upon the mapping method to be used. The probes can be either RNA or DNA probes, and mapping is performed using RFLP, RAPD, or microsatellite technology.

In a particular embodiment, DNA probes are used for RFLP markers. Such probes can come from, for example, Pst I-cloned genomic libraries, and the cloned inserts used as probes may be amplified, for example by PCR, LCR, NASBA™, or other amplification methods recognized in the art. For example, the markers useful in a preferred embodiment of the invention include the following: pA85a, php02302a, php02340a, pk400a, pt155a, pBLT24a, php05180a, pSAC3a, or pA111b for linkage group A; php02366a, php02361a, UBC440a, pK69a, or pL50b for linkage group G; and pA226a, pA715a, pk24a, pB157b, php02275a, UBC379a, OPC-04a, or php02301a for linkage group M. Of course it will be apparent to those skilled in the art that other markers which map to loci for SCN resistance may be utilized in the practice of the invention. For RFLP mapping, restriction fragments are generated using specific restriction enzymes, and the digestion, electrophoresis, Southern transfers and nucleic acid hybridizations are conducted according to art-recognized techniques. See, e.g., Keim et al., Theor. Appl. Genet. 77:786–792, 1989, the disclosures of which are hereby incorporated herein by reference.

In an alternative embodiment of the method of the invention, RAPD technology can be utilized for genetic mapping. A DNA preparation is amplified using art-recognized amplification techniques, and suitable nucleic acid markers are used; for example, UBC440 for linkage Group G and UBC379a and OPC-04a for linkage Group M.

In a soybean breeding program, the method of the present invention envisions the use of marker-associated selection for one or more loci at any stage of population development in a two-parent population, multiple parent population, or a backcross population. Such populations are described in Fehr, W. R. 1987, *Breeding Methods for Cultivar Development*, in J. R. Wilcox (ed.) *Soybeans: Improvement, Production, and Uses*, 2d ed., the disclosures of which are hereby incorporated herein by reference.

Marker-assisted selection according to art-recognized methods may be made, for example, step-wise, whereby the different SCN resistance loci are selected in more than one generation; or, as an alternative example, simultaneously, whereby all three loci are selected in the same generation. Marker-assisted selection for SCN resistance may be done before, in conjunction with, or after testing and selection for other traits such as seed yield.

The DNA from target populations may be obtained from any plant part, and each DNA sample may represent the genotype of single or multiple plant individuals (including seed).

Marker-assisted selection may also be used to confirm previous selection for SCN race-3 resistance or susceptibility made by challenging plants with soybean cyst nematodes in the field or greenhouse and scoring the resulting phenotypes.

The following examples are offered by way of illustration and not by way of limitation.

EXAMPLE 1

Identification of SCN Race 3 Resistance Loci

Materials and Methods
Germplasm Development and Characteristics

A population of 328 recombinant-inbred lines (RILs) was licensed by Pioneer Hi-Bred International, Inc. from Iowa State University and used in this study. This population originated from a cross between two soybean max lines, PI437654 and BSR101, and was developed by single-seed-descent inbreeding from the $F_2$ to the $F_{6:7}$ generation (Baltazar and Mansur, Soybean Genet. Newsl. 19:120–122, 1992; Keim et al., Crop. Sci., in press). PI437654 is a plant introduction from China in the USDA soybean germplasm collection received from the USSR in 1980 (Nelson et al, USDA-ARS Tech. Bull. 1726, 1988). It is in Maturity Group III and resistant to all known races of SCN. BSR 101 was developed at Iowa State University and is in Maturity Group I and susceptible to SCN (Tachibana et al., Crop Sci. 27:612, 1987). At the I locus, PI437654 carries the i allele for black or imperfect black seed, and BSR101 carries the $i^i$ allele for yellow or green seed. The RIL population was scored for these alleles and the I locus was mapped as a marker.

Soybean-Cyst-Nematode Screening

SCN race-3 resistance screening was conducted in a greenhouse using a homogeneous field population of SCN race-3 obtained from the Ames Plantation, near Grand Junction, Tenn. (courtesy of Dr. L. D. Young, USDA-ARS, Jackson, Tenn.). This race-3 isolate was increased and maintained for approximately 60 generations on roots of the standard susceptible cultivar, Essex, in a greenhouse at the Delta Center, University of Missouri, Portageville. In standardized host trials, it averaged 3, 1, 4, 4, and 186 white females (cysts) per plant on Peking, PI90763, PI88788, Picket 71, and Essex, respectively.

Ten plants from each of 298 $F_{6:7}$ RILs of the PI437654 X BSR101 population were evaluated against SCN race-3 in batches of 30 RILs and the five host differentials. The inoculation and evaluation methods were as previously described (Rao-Arelli and Anand, Crop Sci. 28:650–652, 1988; Rao-Arelli et al., Plant Dis. 75:594–595, 1991). Thirty days after inoculation, plant roots were washed and dislodged white females were counted under a stereomicroscope. Index of Parasitism (IP) was calculated for each RIL as a percentage of the cysts on Essex using the formula:

$$IP = \frac{\text{Avg. No. of cysts per RIL}}{\text{Avg. No. of cysts per Essex (susceptible)}} \times 100$$

Laboratory Methods

The DNA of soybean material was extracted using the CTAB method (Murray and Thompson, Nucl. Acids Rev. 8:4321–4325, 1980; Keim et al., Soybean Genet. Newsl. 15:150–152, 1988), with the following modifications. The lyophilized tissue was powdered by adding 2.5g of glass beads (Fisher cat. #11-312A) and 750 mg of tissue in a 50 mL tube and shaking in a paint-can shaker. The concentration of CTAB (hexadecyltrimethyl-ammonium bromide) in the extraction and precipitation buffers was reduced from 1% to 0.5%. After the DNA was precipitated with CTAB, the DNA pellet was dissolved in 2 mL 1M NaCl with shaking at 65° C., 200 rpm, for 2–3 hr. The DNA was re-precipitated by adding 4.5 mL ice cold 95% EtOH. The spooled DNA was washed with 1 mL of 65%, then 1 mL of 85% EtOH, to further remove salts. After the EtOH washes, the DNA was dissolved in 500–1000 uL TE (10,1) and stored at 4° C. until used.

The DNA probes used for RFLP markers came from PstI-cloned genomic libraries as described by Keim and Shoemaker (Soybean Genet. Newsl. 15:147–148, 1988) and cDNA libraries (U.S.D.A.-A.R.S., Beltsville, Md.). The cloned inserts used as probes were amplified by the polymerase chain reaction. Oligonucleotides of the $T_3$ and $T_7$ promoter regions of the phagemid vector pBS$^\pm$ were used as amplification primers. The restriction enzymes EcoRI, HindIII, EcoRV, DraI, TaqI, and HaeIII were used to digest the parental and population DNA. Six hundred sixty-three RFLP markers were used against PI437654 and BSR101 to identify and map 306 RFLP markers segregating in the RIL population. The DNA digestions, electrophoresis, Sou them transfers, and DNA hybridizations were conducted as previously described (Keim et al., Theor. Appl. Genet. 77:786–792, 1989).

Statistical analyses

An analysis o f variance for the IP from 10 replications (single plants) an d 298 treatments (RILs) was used to calculate a broad-sense heritability estimate for resistance using the formula:

$$\text{Heritability} = \frac{MS_{entry} - MS_{error}}{MS_{entry}}$$

where $MS_{entry}$ is the mean square of RILS and $MS_{error}$ is the mean square of residual error.

Genetic linkages and distances between markers were estimated by maximum likelihood analysis of segregating RFLP-marker patterns in the RIL population, using the computer program MAPMAKER/EXP 3.0 (Lincoln et al., Whitehead Inst. Biomed. Res., 1993). A maximum likelihood test was conducted at each marker position to identify those markers significantly (LOD>3.0) associated with phenotypic variation in SCN race-3 reaction using the computer program MAPMAKER/QTL (Lincoln and Lander, Whitehead Inst. Biomed. Res., 1990). Because this population was inbred, having a high degree of homozygosity, only additive genetic effects were estimated.

Results

Heritability

The broad-sense heritability determination of 0.97 for IP indicated the number of cysts per plant within inbred lines was highly consistent. With heritability high, non-genetic variation was well controlled and genetic loci contributing to phenotypic variation could be more accurately detected with markers.

Locations of three SCN race-3 resistance loci

Figure 1:
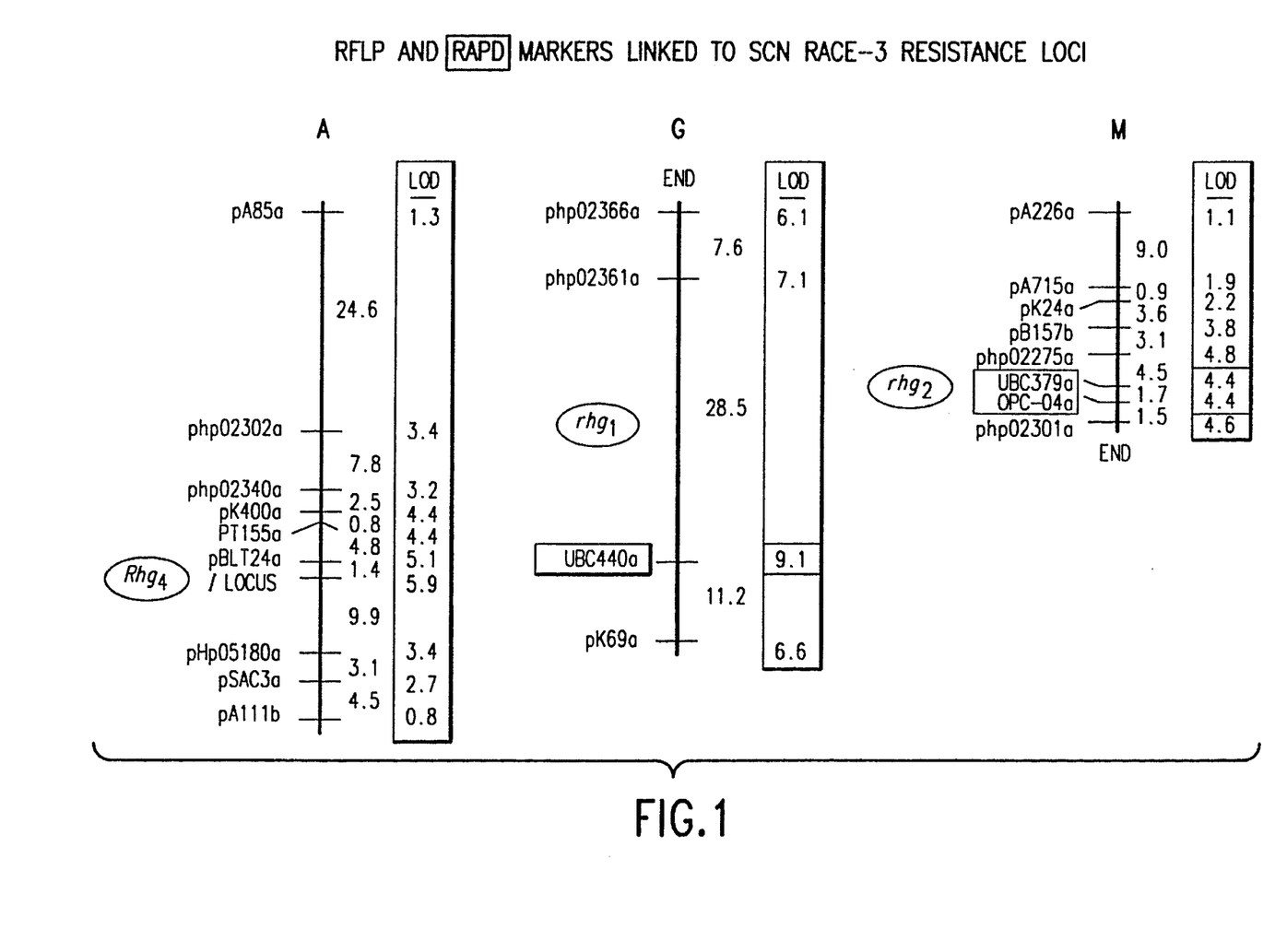
FIG. 1 shows RFLP and RAPD markers linked on SCN race-3 resistance loci. Groups A, G and M are presented, with RFLP and RAPD markers to the left of the groups (RAPD markers are enclosed in boxes). To the right of the group appear distances (in centimorgans) and LOD scores (enclosed in boxes).

Three independent marker loci, the I locus, php02361a, and php02275a, had LOD scores greater than 3.0 for association with SCN race-3 resistance. These markers were located on RFLP linkage groups A, G, and M, respectively (FIG. 1). We estimated the approximate map positions for resistance quantitative-trait-loci (QTL) based on the size of marker-QTL LOD scores and the distances between markers. The resistance QTL on G and M were each clearly placed between two markers because those markers had the highest LOD scores on those groups. However, the resistance QTL on A could not be clearly placed between the I locus and an adjacent marker because, though pBLT24a had the second highest LOD score on that group, the QTL could be on either side of the I locus and still be closer to pBLT24a than to php05180a (FIG. 1).

Level of resistance

Fifty-five of the 298 lines had complete resistance (IP<2%) to SCN race-3. Eleven more lines had IP scores of 5–10%, but these lines did not carry resistance alleles at all three loci (indicated by flanking-marker scores) so were not counted as resistant. This is contrary to a commonly used classification system where resistance is defined as an IP less than 10% (Golden et al., Plant Dis. Rep. 54:544–546, 1970).

Thirty-eight resistant lines were expected in this inbred population provided three genes were needed and had normal (1:1) segregation ratios. This difference from the expected had a chi square ($X^2$) of 7.6, significant at P<0.01. Most markers in this experiment had equivalent numbers of alleles from each parent (data not shown). However, either by chance or natural or unintentional selection, the markers around the resistance locus on M had approximately twice as many alleles from PI437654 as from BSR101. This alone can explain the higher number of expected resistant lines. Assuming PI437654 allele frequencies of 0.5, 0.5, and 0.67 at the resistance loci on A, G, and M, respectively, we would expect 50 resistant lines, which is not significantly different ($X^2 = 0.5$, P<0.01) than the 55 found.

locus on G and to any combination of resistance alleles at two of the three loci.

Complete, or nearly complete, resistance to SCN race-3 was obtained in all 21 lines having the PI437654 marker-type (B) at the six RFLP markers flanking the three loci (Table 1). These same 21 lines had either black or imperfect-black seed-coat types, requiring the i allele at the I locus; thus the i allele was closely linked in coupling to the $Rhg_4$ resistance allele.

TABLE 1

Index of parasitism scores and seed-coat type of
PI437654 × BSR101 recombinant-inbred lines having the PI437654
marker score (B) at six RFLP markers flanking the SCN race-3
resistance loci mapped to linkage groups A, G, and M

| | | | Marker Score | | | | | |
|---|---|---|---|---|---|---|---|---|
| | | | A | | G | | M | |
| Line | IP (%)[a] | Seed Type[b] | pBLT24a | php 05180a | php 02361a | pK69a | php 02275a | php 02301a |
| 3 | 1.1 | ibl | B | B | B | B | B | B |
| 10 | 0.0 | bl | B | B | B | B | B | B |
| 22 | 0.6 | ibl | B | B | B | B | B | B |
| 66 | 0.0 | ibl | B | B | B | B | B | B |
| 79 | 0.0 | bl | B | B | B | B | B | B |
| 93 | 0.0 | bl | B | B | B | B | B | B |
| 96 | 0.0 | bl | B | B | B | B | B | B |
| 114 | 0.0 | ibl | B | B | B | B | B | B |
| 125 | 0.5 | ibl | B | B | B | B | B | B |
| 128 | 0.0 | bl | B | B | B | B | B | B |
| 130 | 0.5 | bl | B | B | B | B | B | B |
| 178 | 0.0 | bl | B | B | B | B | B | B |
| 193 | 0.6 | bl | B | B | B | B | B | B |
| 202 | 0.6 | bl | B | B | B | B | B | B |
| 203 | 0.0 | bl | B | B | B | B | B | B |
| 214 | 0.0 | ibl | B | B | B | B | B | B |
| 218 | 0.6 | bl | B | B | B | B | B | B |
| 221 | 0.0 | bl | B | B | B | B | B | B |
| 265 | 0.9 | bl | B | B | B | B | B | B |
| 271 | 0.0 | ibl | B | B | B | B | B | B |
| 299 | 1.1 | ibl | B | B | B | B | B | B |

[a] IP < 2% considered completely resistant
[b] bl = black; ibl = imperfect black The genetic interval between QTL-flanking markers on G (php02361a to pK69a) was 39.7 cM, compared to 11.3 cM on A (pBLT24a to php05180a) and 7.7 cM on M (php02275a and php02301a) (FIG. 1). Despite this increased interval, both markers flanking the resistance locus on G had higher LOD scores for marker-trait associations than did any markers on A and M. The detection of a QTL effect by marker analysis is a function of both the QTL expression and the distance between QTL and markers. Having higher LOD scores at markers on G despite more recombination between the resistance locus and markers, indicates the locus on G has greater effect on SCN resistance than the resistance loci on A and M. Also, the average IP score for the ABA genotypic class, carrying a resistance allele (B) only at the locus on G, was less than for the classes BAA and AAB, where a resistance allele is carried only on A or M, respectively (FIG. 2).

Figure 2:
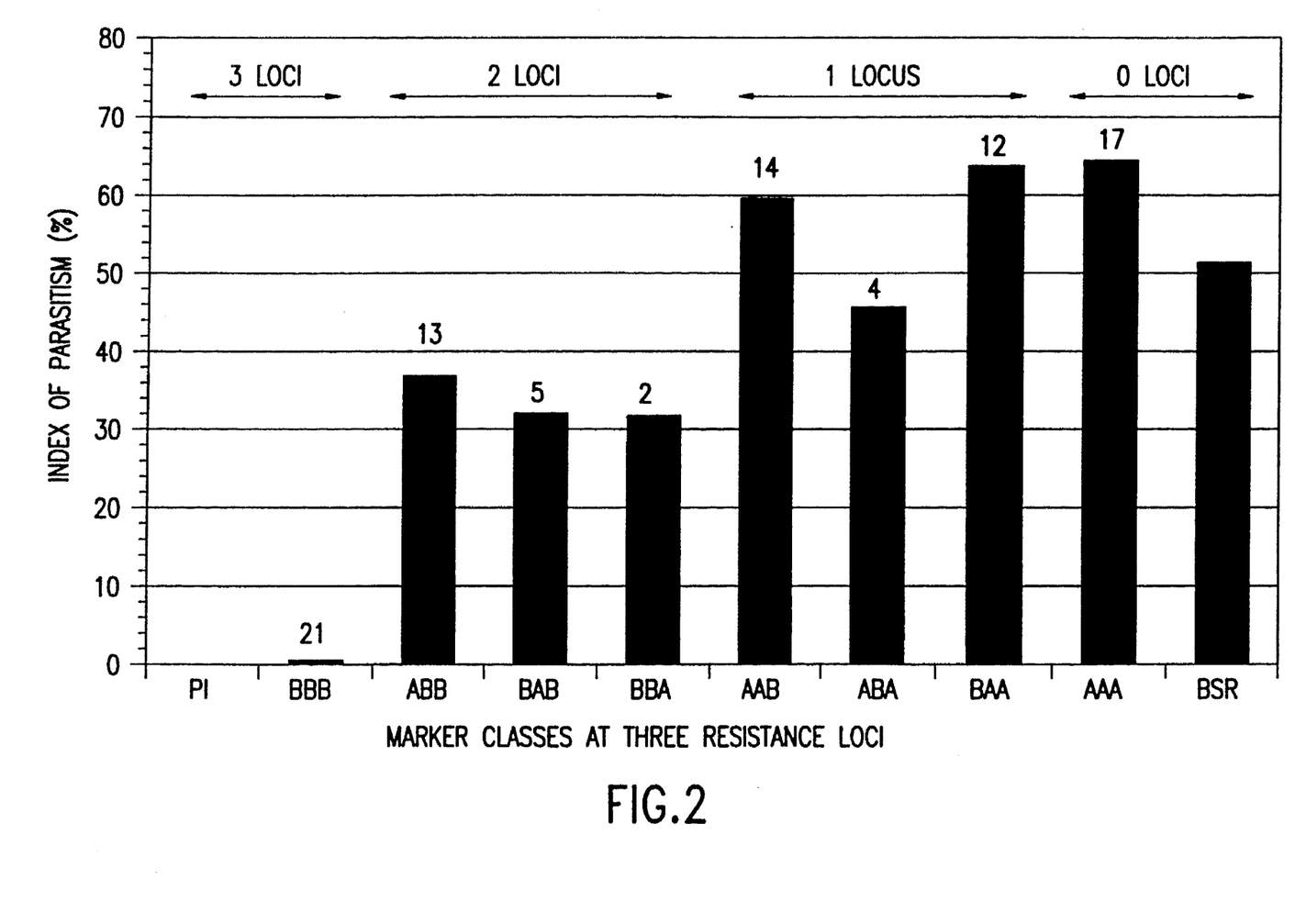
FIG. 2 presents a histogram correlating index of parasitism (as percent of cysts on the variety Essex) with marker classes at three resistance loci.

Lines having a resistance allele only on A or M had approximately the same number of cysts as lines having no resistance alleles at any loci, and lines having resistance alleles at any two of the three loci averaged fewer cysts than lines having resistance alleles at one or no loci (FIG. 2). Partial resistance seems to be attributable to the resistance Nomenclature of SCN race-3 loci Three independent loci necessary for complete resistance to SCN race-3 were genetically mapped in the soybean PI437654. Myers and Anand (Euphytica 55:197–201, 1991) found four of 48 $F_3$ families from the cross PI437654 X Essex resistant to SCN race-3, a proportion that approximates a three-gene system. In that same study, the segregation ratio of $F_2$ plants indicated one locus was dominant and two loci were recessive. The soybean varieties Peking and PI90763 also have one dominant and two recessive resistance loci for SCN race-3, (Rao-Arelli et al., Crop. Sci. 32:862–846, 1992). All progeny from crosses between Peking, PI90763, and PI437654 are resistant to SCN race-3; therefore, the SCN race-3 resistance alleles in these three varieties are at the same three loci (Rao-Arelli and Anand, Crop. Sci. 28:650–652, 1988; Myers and Anand, Euphytica 55:197–201, 1991; Rao-Arelli et al., Crop. Sci. 32:862–864, 1992).

Matson and Williams (Crop Sci. 5:477, 1965) reported a dominant SCN resistance locus, they named $Rhg_4$, about 0.35 recombination units from the I locus was the closest marker associated with a resistance locus on linkage group A (LOD score 5.9, FIG. 1). We assigned $Rhg_4$ to this resistance locus on our map because Peking and PI437654 have the same three SCN race-3 resistance loci and in each variety one locus is dominant. We could not confirm the gene action of any resistance loci because the population we used was inbred; however, given the overall similarity between SCN race-3 resistance in both PI437654 and Peking, we believe $Rhg_4$ is the dominant locus in PI437654.

Caldwell et al., (Agron. J. 52:635–636, 1960) identified three recessive loci, $rhg_1$, $rhg_2$, and $rhg_3$, in Peking for SCN race-1 resistance. Later, Rao-Arelli et al., (Crop, Sci. 32:862–864, 1992) assigned $rhg_1$ and $rhg_2$ to the two recessive loci for SCN race-3 resistance found in Peking, and selected $rhg_2$ to be the recessive resistance locus also found in the soybean PI88788. Because different SCN races were used, the $rhg_1$ and $rhg_2$ designations may have been assigned to different loci in each study. It is unknown whether the same two loci govern both SCN race-1 and race-3 resistance. We have added genetic map information to the identification of the two resistance loci found on G and M in PI437654 and Peking. We propose that the locus on G be $rhg_1$ and the locus on M be $rhg_2$. As more map data becomes available for different sources of SCN resistance and different SCN races, the map locations and locus names assigned here can be referenced to determine when loci are in common and when to name new loci.

Comparison to previous RFLP mapping studies

Many of the RFLP markers in this study have been used by others, and some have been previously associated with the I locus and SCN race-3 resistance. Keim et al., (1990) linked pT153 (pT153 equals pT155 in band pattern and two map locations) and pA111 to the I locus. Our genetic distances between these markers and the I locus were comparable to theirs.

Using PI209332 as the source of SCN resistance, Concibido et al., (Crop Sci., in press) found pA85 on group A significantly associated with SCN race-3 resistance, while pA111 on the same group was not. Our results with these two markers were similar, with pA85 having a higher LOD score than pA111 (FIG. 1). However, pA85a on our map was 41.9 cM from the I locus compared with the 10.9 cM found by Concibido et al. We placed five additional markers between pA85 and the I locus, of which pBLT24 was the nearest RFLP marker to $Rhg_4$.

Boutin, et al.,(Soybean Genet. Newsl. 19:123–127, 1992) and later Concibido, et al. (Crop Sci., in press) reported pK69 on either linkage group B or G associated with SCN race-3 resistance in PI209332. We show that this marker is associated with a resistance locus on group G (FIG. 1). pK69 had been an end marker of group G (formerly linkage group D, Diers, et al. (Theor. Appl. Genet. 83:608–612, 1992)), and we found $rhg_1$ outside this linkage group of markers. We placed two new RFLP markers beyond pK69 and $rhg_1$, thereby marking $rhg_1$ from both sides (FIG. 1).

Concibido, et al. (Crop Sci., in press) also reported the marker pB32 associated with SCN race-3 resistance in PI209332, but were unsure of the linkage group. It is believed pB32 can hybridize to four loci, two of which were mapped in these experiments to linkage groups J and K and were not associated with SCN race-3 resistance. They may have used one of the other two possible marker-loci for this probe. Their pB32 marker was linked to a pK417 marker, which was less significantly associated with SCN resistance. pK417 markers have been mapped to linage groups A, K, and M on the USDA/Iowa State University public RFLP map. We did not use pK417, but comparing our map with the ISU public map, the pK417 markers on both A and M appear near enough to possibly detect linkage to the SCN resistance loci on either of those groups. PI209332 may have a different mode of SCN race-3 resistance than PI437654. Rao-Arelli, et al. (Agronomy Abstracts, 1993) reported that the SCN race-3 resistance in PI209332 is likely controlled by two loci, one dominant and one recessive. If so, evidence from Concibido, et al. (Crop Sci., in press) indicates those two loci are on linkage groups A and G, and the pB32 marker used by them would therefore go to group A.

Marker-assisted selection

The markers used in these experiments, or similarly placed markers, on groups A, G, and M can be used for marker-assisted selection of SCN race-3 resistance in soybean breeding. In this population, 21 lines have the PI437654 marker type at six markers flanking the three resistance loci, and all have virtually complete resistance to SCN race-3 (Table 1). However, all 21 lines also have black or imperfect black seed coat types which are undesirable for breeding. The linkage between the I locus and $Rhg_4$ has been broken and $Rhg_4$ moved into adapted germplasm, most recently with the release of the variety Hartwig which has both PI437654 and Peking in its pedigree (Anand, Crop Sci. 31:856, 1991). Though three loci would provide complete resistance to SCN race-3, partial resistance may be obtained by selecting resistant marker types for any two of the three resistance loci (FIG. 2).

Given that PI437654, Peking, and PI90763 have the same resistance loci for SCN race-3, markers linked to these loci should be useful for marker-assisted selection in germplasm related to these sources, and other sources that are shown to have the same resistance loci. However, PI88788, another common source of SCN race-3 resistance, lacks a resistance allele at either G or M and has a resistance allele at a different locus than does Peking (Rao-Arelli, et al., Crop Sci. 32:862–864, 1992) and PI437654. That unique resistance locus can be genetically mapped to identify the necessary markers for marker-assisted selection of all three SCN race-3 resistance loci in populations related to PI88788.

EXAMPLE 2

RAPD PROTOCOL AND MARKERS

In using RAPD technology for mapping SCN resistance loci, the following markers were utilized:

| Public Primer Name | Linkage Group | Primer Sequence | Mapped Fragment Sizes (kb) |
|---|---|---|---|
| UBC440 | G | CTG TCG AAC C | 0.38; N* |
| UBC379 | M | GGG CTA GGG T | 0.50; N |
| OPC-04 | M | CCG CAT CTA C | 1.05; N |

*N means "null" or no fragment

The following procedure was followed for performing RAPD mapping:

RAPD PROTOCOL

1. Thaw primers, DNA templates, 10×buffers, $MgCl_2$, dNTPs
2. Amplification reaction mix (25 μl reaction):

| Reagent | Stock Conc. | Reaction Conc. | Reaction Vol. |
|---|---|---|---|
| $MgCl_2$ | 25 mM | 4 mM | 4 μl |
| dNTP | 1 mM | 0.2 mM | 5 μl |

-continued

| Reagent | Stock Conc. | Reaction Conc. | Reaction Vol. |
|---|---|---|---|
| Buffer | 10X | 1X | 2.5 μl |
| Enzyme | 10 units/μl | 2.5 units | 0.25 μl |
| $H_2O$ (HPLC grade) | | | |
| Primer | 2 μM | 0.2 μM | 2.5 μl |
| DNA Template | 12.5 ng/μl | 1 ng/μl | 2 μl |

3. Add DNA template or primer to eppendorph tubes or 96-well PCR plate. (It is important not to add both the template and primer to the reaction mix.)
4. Make reaction mix ($MgCl_2$, dNTP, buffer, $H_2O$, primer or template) and mix well.
5. Add enzyme (Stoeffel Fragment) to reaction mix and mix gently.
6. Add master mix to eppendorph tubes or PCR plate.
7. Add one drop light mineral oil to reach reaction, cover and place in thermal cycler.
8. Thermal Cycler program (45 cycles)
   94° C. 1 min
   36° C. 1 min
   36°→>72° ramp 1° C./2 sec
   72° C. 2 min
9. After amplification add 4 μl loading buffer to each reaction.
10. Load 12.5 ul of each reaction into wells of an agarose gel (100 ml gel 2.0% NuSieve 3:1 agarose; 0.1M TAE). Load 123 bp size standard along with samples. Electrophorese for 180 volt-hours.

Although the foregoing invention has been described in detail for purposes of clarity and understanding, it will be clear to those skilled in the art that certain modifications may be practiced within the scope of the appended claims.

What is claimed is:

1. A method of reliably and predictably introgressing soybean cyst nematode resistance into non-resistant soybean germplasm comprising using one or more nucleic acid markers for marker assisted selection among soybean lines to be used in a soybean breeding program, wherein the nucleic acid markers are pA85a, php02302a, php02340a, pk400a, pt155a, pBLT24a, php05180a, pSAC3a, pA11116, php02366a, php02361a, UBC440a, pk69a, pL50b, pA226a, pA715a, pk24a, pB157b, php02275a, UBC379a, OPC-04a, or php02301a; further comprising introgressing said resistance into said non-resistant soybean germplasm.

2. The method of claim 1 wherein the source of soybean cyst nematode resistance is PI437654 or a descendant thereof.

3. The method of claim 1 wherein the source of soybean cyst nematode resistance is Peking or a descendant thereof.

4. The method of claim 1 wherein the source of soybean cyst nematode resistance is PI90763 or a descendant thereof.

5. The method of claim 1 wherein the marker assisted selection comprises the use of restriction fragment length polymorphism analysis.

6. The method of claim 1 wherein the marker assisted selection comprises the use of RAPD analysis.

7. The method of claim 1 wherein the marker assisted selection comprises the use of microsatellite analysis.

8. A quantitative trait locus associated with resistance to soybean cyst nematode race-3, said locus mapping to soybean linkage group A, and mapped by one or more of markers pA85a, php02302a, php02340a, pk400a, pT155a, pBLT24b, php05180a, pSAC3a, and pA111b.

9. A quantitative trait locus associated with resistance to soybean cyst nematode race-3, said locus mapping to soybean linkage group G, and mapped by one or more of markers php02366a, php02361a, UBC440a, pk69a, UBC576a, and pL50b.

10. A quantitative trait locus associated with resistance to soybean cyst nematode race-3, said locus mapping to soybean linkage group M, and mapped by one or more of markers pA226a, pA715a, pk24a, pB157b, php02275a, UBC379a, OPC-04a, and php02301a.

* * * * *

UNITED STATES PATENT AND TRADEMARK OFFICE
CERTIFICATE OF CORRECTION

PATENT NO.   : 5,491,081
DATED        : February 13, 1996
INVENTOR(S)  : David M. Webb It is certified that error appears in the above-identified patent and that said Letters Patent is hereby corrected as shown below:

Column 4,
Line 16, after "M.", insert:

-- The Pioneer Hi-Bred International, Inc. proprietary nucleic acid markers have been deposited with the ATCC and are as follows: php02366 assigned ATCC 69934; php02340 assigned ATCC 69935; php02361 assigned ATCC 69936; php02301 assigned ATCC 69937; php05180 assigned ATCC 69938; php02275 assigned ATCC 69937; and php02302 assigned ATCC 69940. The other, non-proprietary probes are available from Linkage Genetics, Salt Lake City, Utah, and from Biogenetic Services, Brookings, South Dakota. --

Column 11,
Line 31, insert:

-- DEPOSIT STATEMENT

A deposit of the Pioneer Hi-Bred International, Inc. proprietary nucleic acid markers disclosed above and recited in the appended claims has been made with the American Type Culture Collection (ATCC), 12301 Parklawn Drive, Rockville, Maryland 20852. The date of deposit was October 19, 1995. The markers deposited were taken from the same deposit maintained by Pioneer Hi-Bred International, Inc. since prior to the filing date of this application. All restrictions upon the deposit have been removed, and the deposit is intended to meet all of the requirements of 37 C.F.R. § 1.801-1.809.

UNITED STATES PATENT AND TRADEMARK OFFICE
CERTIFICATE OF CORRECTION

PATENT NO. : 5,491,081
DATED : February 13, 1996
INVENTOR(S) : David M. Webb It is certified that error appears in the above-identified patent and that said Letters Patent is hereby corrected as shown below:

Column 11, cont'd.,
The markers deposited and their respective ATCC accession numbers are as follows: php02366 assigned ATCC 69934; php02340 assigned ATCC 69935; php02361 assigned ATCC 69936; php02301 assigned ATCC 69937; and php05180 assigned ATCC 69938; php02275 assigned ATCC 69937; and php02302 assigned ATCC 69940. The deposit will be maintained in the depository for a period of 30 years, or 5 years after the last request, or for the effective life of the patent, whichever is longer, and will be replaced as necessary during that period. --

Signed and Sealed this

Tenth Day of August, 2004

JON W. DUDAS
*Acting Director of the United States Patent and Trademark Office*